Figure 2:

United States Patent [19]
Cherukuri et al.

[11] Patent Number: 5,549,917
[45] Date of Patent: Aug. 27, 1996

[54] FLASH FLOW FORMED SOLLOID DELIVERY SYSTEMS

[75] Inventors: Subraman R. Cherukuri, Towaco, N.J.; Gerald E. Battist, Reston; James H. Perkins, Boyce, both of Va.

[73] Assignee: Fuisz Technologies Ltd., Chantilly, Va.

[21] Appl. No.: 487,794

[22] Filed: Jun. 7, 1995

Related U.S. Application Data

[62] Division of Ser. No. 269,679, Jul. 1, 1994.

[51] Int. Cl.$^6$ .............................. A23L 1/05; A23L 1/221; A23P 1/04
[52] U.S. Cl. .............................. 426/96; 426/99; 426/103; 426/658; 426/516; 426/573; 424/458
[58] Field of Search .............................. 426/573, 96, 99, 426/302, 306, 103, 516, 658, 573

[56] References Cited

U.S. PATENT DOCUMENTS

| | | |
|---|---|---|
| Re. 32,016 | 10/1985 | Esders et al. . |
| 796,528 | 8/1905 | Pollack . |
| 816,055 | 3/1906 | Zoeller . |
| 847,366 | 3/1907 | Pollock . |
| 856,424 | 6/1907 | Robinson . |
| 1,489,342 | 4/1924 | Brent . |
| 1,541,378 | 6/1925 | Parcell . |

(List continued on next page.)

FOREIGN PATENT DOCUMENTS

| | | |
|---|---|---|
| 609135 | 4/1988 | Australia . |
| 609137 | 4/1988 | Australia . |
| 900605 | 11/1977 | Belgium . |
| 1303511 | 4/1988 | Canada . |
| 0287488A1 | 3/1988 | European Pat. Off. . |
| 0387950A1 | 8/1990 | European Pat. Off. . |
| 86052 | 4/1988 | Israel . |
| 86053 | 4/1988 | Israel . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |
| 519858 | 5/1971 | Switzerland . |
| 489211 | 7/1986 | Switzerland . |
| 2155934B | 3/1985 | United Kingdom . |
| WO91/18613 | 5/1991 | WIPO . |

OTHER PUBLICATIONS

R. H. Doremus, "Crystallization of Sucrose From Aqueous Solution," *Journal of Colloid and Interface Science*, 104, pp. 114–120 (1985).
P. Bennema, "Surface Diffusion and the Growth of Sucrose Crystals," *Journal of Crystal Growth*, 3,4 pp. 331–334 (1968).
T. D. Simpson, et al., "Crystalline Forms of Lactose Produced in Acidic Alcoholic Media," *Journal of Food Science*, 47, pp. 1948–1954 (1982).
A. D. Randolph, et al., "Continuous Sucrose Nucleation," *The International Sugar Journal*, pp. 8–12 (1974).
K. B. Domovs, et al., "Methanol–Soluble Complexes of Lactose and of other Carbohydrates," *J. Dairy Science*, 43, pp. 1216–1223 (1960).
A. D. Randolph, et al., "Continuous Sucrose Nucleation," *The International Sugar Journal*, pp. 35–38 (1974).
A. D. Randolph, et al., "Coninuous Sucrose Nucleation," *The International Sugar Journal*, pp. 73–77 (1974).
ICI Americas, Inc., "ICI Americas Products for Cosmetics and Pharmaceuticals," (1977).
Domino Sugar Corporation, "Co-crystallization".
Domino Sugar Corporation, "Raspberry".
Domino Sugar Corporation, "Molasses Dark".

*Primary Examiner*—Jeanette M. Hunter
*Attorney, Agent, or Firm*—Hoffmann & Baron

[57] ABSTRACT

Discrete entities of a solid suspension are made from a solid fat matrix and a non-fat solid substrate having an active associated with said substrate. These entities are spheroidal in shape, have uniform size and substantially the same active content due to the flash flow process used to make them. They are especially useful as delivery systems for comestibles, pharmaceuticals and personal products.

40 Claims, 2 Drawing Sheets

U.S. PATENT DOCUMENTS

| | | |
|---|---|---|
| 2,826,169 | 3/1958 | Le Veen . |
| 2,918,404 | 12/1959 | Mende et al. . |
| 3,019,745 | 2/1962 | Du Bois et al. . |
| 3,036,532 | 5/1962 | Bowe . |
| 3,067,743 | 12/1962 | Merton et al. . |
| 3,070,045 | 12/1962 | Bowe . |
| 3,073,262 | 1/1963 | Bowe . |
| 3,095,258 | 6/1963 | Scott . |
| 3,118,396 | 1/1964 | Brown et al. . |
| 3,118,397 | 1/1964 | Brown et al. . |
| 3,125,967 | 3/1964 | Bowe . |
| 3,131,428 | 5/1964 | Mika . |
| 3,308,221 | 3/1967 | Opfell . |
| 3,324,061 | 6/1967 | Tanquary et al. . |
| 3,482,998 | 12/1969 | Carroll et al. . |
| 3,523,889 | 8/1970 | Eis . |
| 3,557,717 | 1/1971 | Chivers . |
| 3,557,718 | 1/1971 | Chivers . |
| 3,595,675 | 7/1971 | Ash et al. . |
| 3,615,671 | 10/1971 | Schoaf . |
| 3,625,214 | 12/1971 | Higuchi . |
| 3,676,148 | 7/1972 | De Weese et al. . |
| 3,686,000 | 8/1972 | Lawrence . |
| 3,723,134 | 3/1973 | Chivers . |
| 3,749,671 | 7/1973 | Gedge et al. . |
| 3,762,846 | 10/1973 | Chivers . |
| 3,766,165 | 10/1973 | Rennhard . |
| 3,856,443 | 12/1974 | Salvi . |
| 3,875,300 | 4/1975 | Homm et al. . |
| 3,876,794 | 4/1975 | Rennhard . |
| 3,882,725 | 5/1975 | Rao et al. . |
| 3,902,351 | 9/1975 | Kreps . |
| 3,907,644 | 9/1975 | Möllering et al. . |
| 3,912,588 | 10/1975 | Möllering et al. . |
| 3,925,164 | 9/1975 | Beaucamp et al. . |
| 3,925,525 | 12/1975 | LaNieve . |
| 3,930,043 | 12/1975 | Warning et al. . |
| 3,951,821 | 4/1976 | Davidson . |
| 3,967,623 | 7/1976 | Butterworth et al. . |
| 3,972,725 | 8/1976 | Nicol . |
| 3,981,739 | 9/1976 | Dmitrovsky et al. . |
| 3,991,766 | 11/1976 | Schmitt et al. . |
| 3,992,265 | 11/1976 | Hansen . |
| 4,056,364 | 11/1977 | Dmitrovsky et al. . |
| 4,072,658 | 2/1978 | Okamoto et al. . |
| 4,086,418 | 4/1978 | Turbak et al. . |
| 4,090,920 | 5/1978 | Studer, Jr. . |
| 4,136,145 | 1/1979 | Fuchs et al. . |
| 4,153,512 | 5/1979 | Messner et al. . |
| 4,159,210 | 6/1979 | Chen et al. . |
| 4,160,696 | 7/1979 | Wu . |
| 4,164,448 | 8/1979 | Röeschlau et al. . |
| 4,166,005 | 8/1979 | Masurekar et al. . |
| 4,168,205 | 9/1979 | Danninger et al. . |
| 4,178,393 | 12/1979 | Gregerson . |
| 4,186,251 | 1/1980 | Tarbutton . |
| 4,194,063 | 3/1980 | Frank et al. . |
| 4,199,373 | 4/1980 | Dwivedi . |
| 4,241,178 | 12/1980 | Esders et al. . |
| 4,271,199 | 6/1981 | Cherukuri et al. . |
| 4,293,292 | 10/1981 | Israel . |
| 4,293,570 | 10/1981 | Vadasz . |
| 4,303,684 | 12/1981 | Pitchon et al. . |
| 4,335,232 | 6/1982 | Irwin . |
| 4,338,350 | 7/1982 | Chen et al. . |
| 4,348,420 | 9/1982 | Lynch et al. . |
| 4,362,757 | 12/1982 | Chen et al. . |
| 4,371,516 | 2/1983 | Gregory et al. . |
| 4,376,743 | 3/1983 | Dees . |
| 4,382,963 | 5/1983 | Klose et al. . |
| 4,382,967 | 5/1983 | Koshida . |
| 4,492,685 | 1/1985 | Keith et al. . |
| 4,496,592 | 1/1985 | Kuwahara et al. . |
| 4,500,546 | 2/1985 | Turbak et al. . |
| 4,501,538 | 2/1985 | Bray . |
| 4,511,584 | 4/1985 | Percel et al. . |
| 4,526,525 | 7/1985 | Oiso et al. . |
| 4,581,234 | 4/1986 | Cherukuri et al. . |
| 4,585,797 | 4/1986 | Cioca . |
| 4,619,833 | 10/1986 | Anderson . |
| 4,684,534 | 8/1987 | Valentine . |
| 4,722,845 | 2/1988 | Cherukuri et al. . |
| 4,747,881 | 5/1988 | Shaw et al. . |
| 4,765,991 | 8/1988 | Cherukuri et al. . |
| 4,772,477 | 9/1988 | Weiss et al. . |
| 4,793,782 | 12/1988 | Sullivan . |
| 4,797,288 | 1/1989 | Sharma et al. . |
| 4,816,283 | 3/1989 | Wade et al. . |
| 4,839,184 | 6/1989 | Cherukuri et al. . |
| 4,846,643 | 7/1989 | Yamamoto et al. . |
| 4,853,243 | 8/1989 | Kahn et al. . |
| 4,855,326 | 8/1989 | Fuisz . |
| 4,867,986 | 9/1989 | Desai et al. . |
| 4,871,501 | 10/1989 | Sugimoto et al. . |
| 4,872,821 | 10/1989 | Weiss . |
| 4,873,085 | 10/1989 | Fuisz . |
| 4,879,108 | 11/1989 | Yang et al. . |
| 4,882,144 | 11/1989 | Hegasy . |
| 4,885,281 | 12/1989 | Hanstein et al. . |
| 4,900,563 | 2/1990 | Cherukuri et al. . |
| 4,931,293 | 6/1990 | Cherukuri et al. . |
| 4,933,192 | 6/1990 | Darling . |
| 4,939,063 | 7/1990 | Tamagawa . |
| 4,978,537 | 12/1990 | Song . |
| 4,981,698 | 1/1991 | Cherukuri et al. . |
| 4,988,529 | 1/1991 | Nakaya et al. . |
| 4,997,856 | 5/1991 | Fuisz . |
| 5,009,893 | 4/1991 | Cherukuri et al. . |
| 5,011,532 | 4/1991 | Fuisz . |
| 5,028,632 | 7/1991 | Fuisz . |
| 5,034,421 | 7/1991 | Fuisz . |
| 5,037,662 | 8/1991 | Poulose et al. . |
| 5,039,446 | 8/1991 | Estell . |
| 5,041,377 | 8/1991 | Becker et al. . |
| 5,057,328 | 10/1991 | Cherukuri et al. . |
| 5,066,218 | 11/1991 | Silver . |
| 5,073,387 | 12/1991 | Whistler . |
| 5,077,076 | 12/1991 | Gonsalves et al. . |
| 5,079,027 | 1/1992 | Wong et al. . |
| 5,082,682 | 1/1992 | Peterson . |
| 5,082,684 | 1/1992 | Fung . |
| 5,084,295 | 1/1992 | Whelan et al. . |
| 5,089,606 | 2/1992 | Cole et al. . |
| 5,094,872 | 3/1992 | Furcsik et al. . |
| 5,096,492 | 3/1992 | Fuisz . |
| 5,104,674 | 4/1992 | Chen et al. . |
| 5,110,614 | 5/1992 | Corbin et al. . |
| 5,164,210 | 11/1992 | Campbell et al. . |
| 5,169,657 | 12/1992 | Yatka et al. . |
| 5,169,658 | 12/1992 | Yatka et al. . |
| 5,171,589 | 12/1992 | Richey et al. . |
| 5,173,317 | 12/1992 | Hartman et al. . |
| 5,173,322 | 12/1992 | Melachouris et al. . |
| 5,175,009 | 12/1992 | Synosky et al. . |
| 5,196,199 | 3/1993 | Fuisz . |
| 5,236,734 | 8/1993 | Fuisz . |
| 5,238,696 | 8/1993 | Fuisz . |
| 5,268,110 | 12/1993 | Fuisz . |
| 5,279,849 | 1/1994 | Fisz et al. . |
| 5,284,659 | 2/1994 | Cherukuri et al. . |
| 5,286,513 | 2/1994 | Fuisz . |
| 5,288,508 | 2/1994 | Fuisz . |
| 5,306,955 | 4/1994 | Fryer . |
| 5,346,377 | 9/1994 | Bogue . |
| 5,348,758 | 9/1994 | Fuisz et al. . |

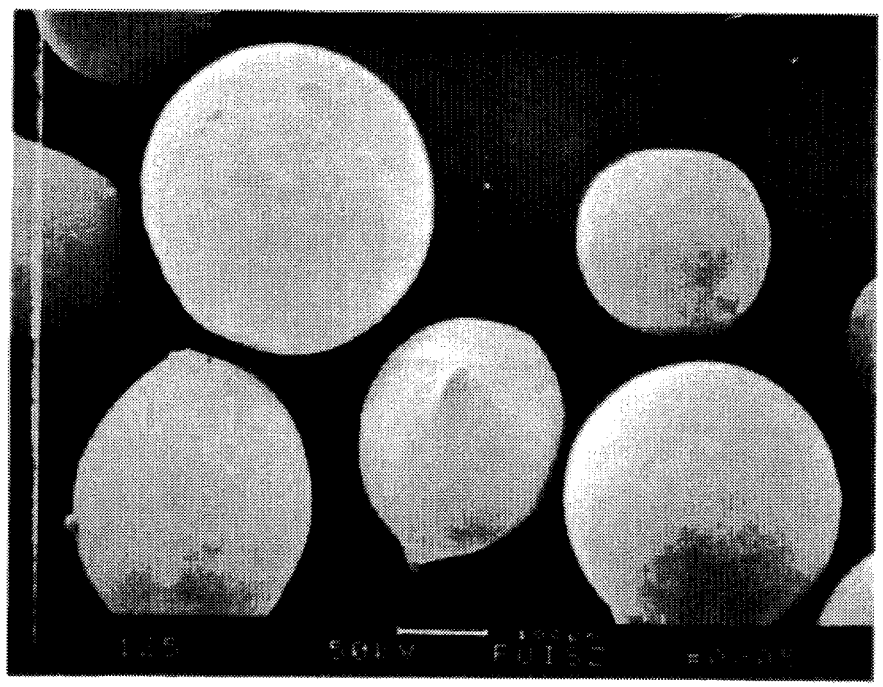
FIG. IA
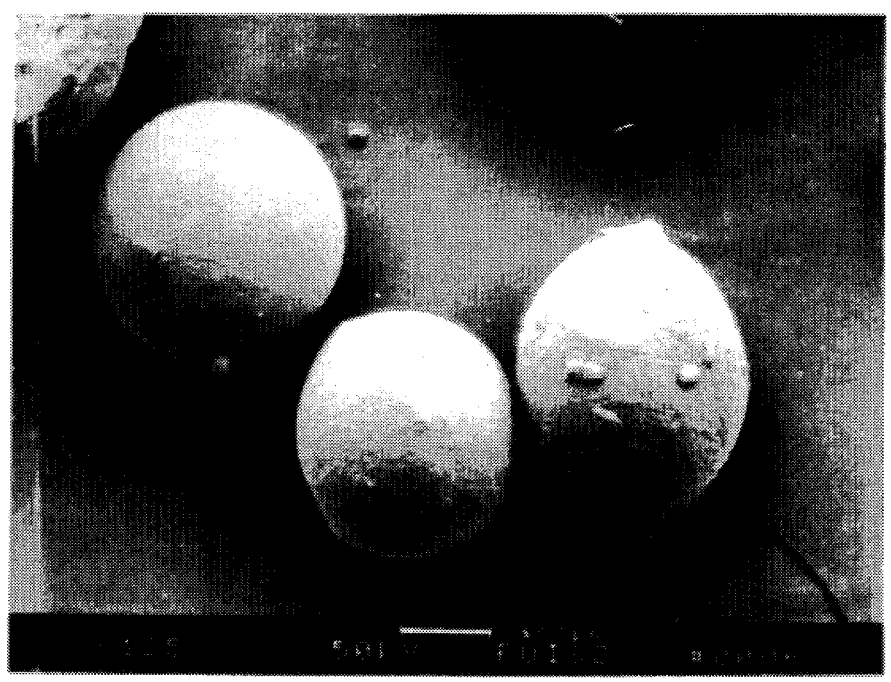
FIG. IB

FLASH FLOW FORMED SOLLOID DELIVERY SYSTEMS

This is a division of U.S. Ser. No. 08/269,679 filed on Jul. 1, 1994.

FIELD OF THE INVENTION

The present invention relates to delivery systems for actives in the form of discrete entities which comprise a solid suspension of a non-fat solid substrate in a solid fat. These entities are formed using flash flow processing in combination with a fluid disruptive force to form discrete spheroids of a solid suspension.

BACKGROUND OF THE INVENTION

The processing of materials using extrusion techniques and spray nozzles has been used for many years. In particular, in the food, cosmetic and pharmaceutical industry, ingestible ingredients have been subjected to a number of different processing techniques whereby the ingredients are transformed from their original structure into a new form. Such transformation is usually through the application of pressure and heat, as well as various solvents.

There are many forms of spray drying which have been used over the years for a variety of applications. In general, spray drying involves the atomization of a feedstock in aqueous solution into a spray, followed by contact with a drying medium, e.g. air, which results in moisture evaporation and dried particles. The atomization of a feed into a spray results in the breakup of the liquid into droplets which are then dried as they are suspended in a medium of warm or hot air. The nozzles from which the spray emanates can be selected from a variety of different shapes and configurations and can produce a number of different effects. For example, the forces emanating from the spray nozzle can be centrifugal, pressure, kinetic or sonic. Nozzles, which are generally conical in shape, can have grooved cores, swirled chambers or other geometric designs which impart a specific effect or character on the liquid as it is forced through the orifice.

These different designs have been studied extensively, with the result being that little is actually understood with respect to the subtleties of droplet formation in spray drying equipment. While a number of theories have been advanced to explain the formation of droplets and their variation, the complexity of droplet formation has defied precise empirical correlation. In fact, depending on the pressure, type of liquid used and nozzle type, only general conclusions have been reported in the literature. Such conclusions include the observation that the discharge velocity of the droplet from the nozzle greatly impacts the fineness and size distribution of the resultant droplets. Additionally, it is recommended by some experts that the best atomization is obtained by keeping the discharge velocity of the liquid from the nozzle above a certain minimum.

In addition to the drying steps involved in standard spray drying processing, spray chilling or spray congealing of materials has also been widely used. For example, it is known to take fats which are solid at room temperature, melt them to a liquid and spray them from a nozzle into a cooled chamber where the droplets solidify. In these processes, the fat is subjected to temperatures for a relatively significant amount of time such that the fat is above its melting point and in the molten state. These conditions are necessary to properly process the fat into congealed droplets and to prevent clogging of the processing equipment.

There are several drawbacks to conventional spray drying or spray congealing methods. First, these processes result in subjecting the material to be processed to a significant heat history, which in the case of heat sensitive materials is unacceptable. For example, in the case of highly volatile flavor oils or heat sensitive sweeteners such as aspartame, exposure to heat causes loss of their ability to fully perform. The same applies to pharmaceuticals which lose their activity if exposed to excessive heat. Additionally, the heating chambers which are required to evaporate the water or other solvent in conventional spray drying methods are costly and inefficient.

Second, spray drying is commonly conducted in aqueous media whereby the water is removed during the drying process. The use of water or other solvents requires extra measures with respect to processing and disposal equipment, all of which also add to the cost of the process and system, and prevents the incorporation of water sensitive materials. Additionally, spray drying is a relatively low output process, requiring high amounts of energy to evaporate the water. This, of course is energy inefficient.

In spray drying and spray congealing processes, the feedstock material is heated to its molten state in a mixing vat and pumped into a feedline which is connected to a nozzle. The feedline and nozzle must be kept at elevated temperature to keep the feed material flowing. In the case of fats which are solid at room temperature, sufficient heat must be applied to keep the fat in the liquid state, both in the mixing vat as well as during its transport to the nozzle head. In the case of spray drying, heat is further applied in the form of hot air which is used to dry the droplets as they emanate from the nozzle.

The application of heat throughout all phases of the conventional spray drying and spray congealing processes is costly and requires control features which must be monitored. Additionally, the amount of space required to conduct the conventional processes is large and therefore costly. This is due to the need for a large volume used to dry or cool the particles, typical of the fluidized bed type processes.

Furthermore, conventional spray drying or spray congealing processes require the feed material to sit for relatively long periods, i.e. hours, in the liquid state while they are waiting to be pumped into the feedlines and subsequently sprayed. This waiting period creates a heat history which, as previously discussed, is deleterious to heat sensitive materials which may be present in the feed material, e.g. volatile flavor oils, heat sensitive sweeteners and pharmaceuticals. Furthermore, the conventional processes require dispersing agents to keep components in the molten mixture from settling out prior to and during pumping to the nozzle.

Additionally, in prior art spray drying or congealing methods variables such as pressure, temperature, nozzle type and material type must be balanced to produce a consistent particle size. These variables are such that it makes predictability of the character of the final product difficult at best to determine. Additionally, even under the best of conditions, uniformity of content of the particles is not necessarily controllable. Particles formed from spray drying or spray congealing can only have uniformity of content if they are the same size and are made from a homogenous mixture of ingredients, i.e. a blend of materials.

More recently, an apparatus and method for processing feedstock has been described by Dr. Richard Fuisz in copending U.S. Ser. No. 07/965,804 entitled "Process For Making Shearform Matrix". This application relates to a unique process and apparatus for making a matrix using fluid shear force. The process involves controlling the temperature of a feedstock which includes a solid non-solubilized carrier material to the point where the feedstock undergoes internal flow. The flowing material is then ejected as a stream under pressure from an orifice which is then disrupted by a fluid shear force as it emanates from the orifice. The fluid shear force is preferably air. This application describes apparatus which is useful in the present invention and is incorporated herein by reference.

The present invention seeks to improve on the prior art techniques of spray drying or spray congealing and overcome the disadvantages associated with these techniques. A new form of product has been discovered using flash flow processing techniques. This new form has been termed a "solloid", the definition of which is discussed further herein. The solloids of the present invention are solid suspensions, i.e. a solid suspended in a solid, which are formed by using flash flow processing and disruptive fluid shear forces to form discrete, uniform spheroids under extremely low pressures as compared to the prior art processes, and with minimal exposure to heat. The present invention seeks to avoid temperatures above those which are necessary to achieve a flow condition of the matrix material being processed, which in most instances will be below or close to the melting point temperature. The temperature required to create the flow condition, however, must not be such that it reaches the melting point of the non-fat solid substrate in the fat matrix. Additionally, the time period during which the feedstock material is subjected to these temperatures is very short, i.e. on the order of tenths of a second in the flash heat method and on the order of seconds in the flash shear method.

SUMMARY OF THE INVENTION

The present invention relates to a method of forming a solid suspension hereinafter termed a "solloid" for delivering actives. The methods includes: a) providing a mixture of a non-fat solid substrate having an active associated therewith and a solid fat which is solidifiable at room temperature and having a flow point lower than the melting point of said non-fat solid substrate; and b) subjecting such mixture to conditions of flash flow wherein such mixture is heated to at least a temperature sufficient to cause said fat to undergo intraparticle flow but below the melting point of the solid substrate and a disruptive force is applied to said heated mixture to cause said mixture to form discrete solloids.

For purposes of the present invention, the term "solloid" will refer to the resultant product formed by subjecting a composition, i.e. a solid non-fat substrate in a solid fat, which has been flash flow processed, to a disruptive force, such as the frictional forces of gas, which disrupts the continuity of the material into discrete spheroidal shaped entities. The term also refers to the product formed by subjecting the above-mentioned composition to conditions of force and temperature sufficient to create intraparticle flow of the fat and applying sufficient fluid disruptive force to create and maintain discrete spheroidal shaped entities of a solid suspension. The solloid is used as a delivery system for actives and is particularly useful in ingestible products such as comestibles and pharmaceuticals, and the like, as well as cosmetics. The compositions of the present invention are of particular use as a delivery system for flavors, sweeteners and acidulants in chewing gum and confectionery compositions.

Additionally, the present invention is directed to a composition of matter which comprises a plurality of solloids. The solloids comprise a solid suspension of a solid non-fat substrate having an active associated therewith dispersed in the material which is solidifiable at room temperature and having an intraparticle flow point lower than the melting point of said solid non-fat substrate. A predominant amount of the solloids have substantially the same active content and at least about 60% or more and preferably about 80% of these solloids have a mean diameter particle size, less than about 300 to about 400 microns.

The process of the present invention utilizes flash flow processing in combination with the application of separate disruptive fluid shear forces which are applied to the feedstock immediately upon reaching the flow condition. It is an important feature of this invention that an intimate mixture of the solid non-fat substrate and the fat be maintained and preserved throughout the process in order to result in the production of solloids. Thus, the application of temperature and initial force are such as to create an internal flow condition of the fat. The disruptive force applied subsequently to create solloids must not be so great as to destroy or separate the solid non-fat substrate suspended in the flowable fat material.

The term flash flow has become recognized in the art as referring to conditions of temperature and force required to transform a solid feedstock having a certain morphological and/or chemical structure, to a new solid having a different morphological and/or chemical structure without subjecting the solids to a heat history or other requirements inherent in extrusion processing. The term flash flow is described in co-owned U.S. Pat. Nos. 5,236,734, issued Aug. 17, 1993 and 5,238,696, issued Aug. 24, 1993, as well as co-pending U.S. Ser. No. 07/787,245 filed Nov. 4, 1991 and U.S. Ser. No. 07/893,238.

The term flash flow refers to subjecting an appropriate feedstock to conditions of temperature and force which induce a solid feedstock to undergo rapidly such physical and/or chemical transformation. The flash flow of the feedstock may be accomplished either by a flash heat process or by a flash shear process.

In the flash heat process a shearform matrix can be formed by spinning a feedstock in a "cotton candy" fabricating type machine. The spinning machine used to achieve a flash heat process can be a cotton candy type machine, such as the Econo Floss Model 3017 manufactured by Gold Metal Products Company of Cincinnati, Ohio, a machine having a coiled heater element as disclosed in U.S. Ser. No. 954,257 filed Sep. 30, 1992 (herein incorporated by reference) and the like. It will be appreciated by those skilled in the art that any apparatus or physical process which provides similar forces and temperature gradient conditions can also be used. For simplicity in disclosing and describing this invention, the term flash heat will be understood to mean a process which includes subjecting a feedstock to the combination of temperature, thermal gradients, flow, flow rates, and mechanical forces of the type produced in a cotton candy machine or the above-referenced U.S. Ser. No. 954,257. The apparatus is operated at the temperature and speed which permits flash heat of the feedstock without deterioration of any of its ingredients.

In the flash heat process, the feedstock material is heated sufficiently to create an internal flow condition which permits part of the feedstock to move at a subparticle level with respect to the rest of the mass and exit openings provided in the perimeter of the spinning head. The centrifugal force created in the spinning head flings the flowing feedstock material outwardly from the head so that it reforms with a changed structure. The force required to discharge flowable feedstock is provided by the forces which result from the spinning head. The flash heat process has been used to produce an amorphous matrix from a crystalline material as disclosed in the aforementioned Fuisz patents. In the present invention, the feedstock comprises a mixture of a solid non-fat substrate and solid fat, which is then subjected to heat sufficient to permit intraparticle flow of the fat. The centrifugal force flings the feedstock material undergoing intraparticle flow into the air where the frictional forces provided by the ambient air disrupt the stream of such material and the newly formed masses and lock the new morphological structure in place. The resultant product is the spheroidal shaped solid suspension referred to as a solloid.

In the flash shear process, a shearform matrix is formed by raising the temperature of the feedstock material, which includes a non-solubilized fat, to a point where said fat undergoes intraparticle flow. The feedstock is advanced and ejected from an extruder or similar type of machinery while the fat is undergoing intraparticle flow and is then subjected to disruptive fluid shear forces to form multiple parts or masses which comprise the individual spheroidal solloids.

The solloids are substantially cooled immediately after contact with the fluid shear force and are permitted to continue in a free-flow or free-fall condition, whereby they are further cooled to prevent individual solloids from adhering to each other and to maintain a free-flow condition.

The feedstock material which can be used in a flash shear process includes but is not limited to a carrier such as fats and other oleaginous materials.

It is important that the feedstock selected for the flash flow process have the ability to be processed without reliance upon dissolution. In the case of fat based materials, the feedstock is a solid material at room temperature, which is then subjected to the flash shear or flash heat process. No solvents or liquids are required to obtain the solloid form in either of the flash shear or flash heat processes. These processes are solid to solid processes which occur rapidly, with little or no heat history during processing.

The flash shear process can be carried out in an apparatus which has means for increasing the temperature of a non-solubilized feedstock and means for simultaneously advancing it for ejection. A multiple heating zone twin extruder can be used for increasing the temperature and advancing feedstock. The second element of the apparatus is a means for ejecting the feedstock in a condition for shearing it to provide the shearform matrix. The means for ejecting is in fluid communication with the means for increasing the temperature and is arranged at the point to receive the feedstock while it is in the internal flow condition. The means for ejecting the feedstock is preferably a nozzle which provides sufficient frictional gas force applied to the ejected feedstock stream to disrupt the stream and form and maintain a solloid.

Apparatus for flash shear processing of the feedstock is described in co-pending U.S. Ser. No. 965,804, filed Oct. 23, 1992. The means for shearing is arranged proximally to the ejector and is disposed to effect the shear of the feedstock while it is in the internal flow condition. Preferably, the means for shearing is the means for delivering fluid such as air at sufficient velocity and at elevated temperature against the feedstock stream as it exits a nozzle. Such a device can be an external atomizing nozzle. The means for shearing can also be a chamber in which the environment can be maintained to induce shear upon the collision of a high velocity of a stream of feedstock directed against a preselected and maintained environment.

BRIEF DESCRIPTION OF THE DRAWINGS

FIG. 1 shows microphotographs of solloids made in accordance with the present invention.

FIG. 2 is a microphotograph of a cross-section of a solloid made in accordance with the present invention.

DETAILED DESCRIPTION AND PREFERRED EMBODIMENTS

As previously discussed, the solloids of the present invention are discrete uniformly shaped spheroidal solid suspension delivery systems. The solid suspension includes a non-fat solid substrate having an active agent associated therewith. The non-fat solid substrate is suspended in a solid fat matrix. The discrete solloids can be used in a variety of products such as pharmaceuticals, comestibles, personal products and the like. The solloids are achievable through flash flow processing which may be either flash shear or flash heat as further described herein. The advantages of the present invention allow for both uniform delivery and controlled release of the active.

The active is generally associated with the non-fat solid substrate usually by simple mixing means. The term "associated with" includes the imbibing of the active into, coating onto or uniting with the non-fat solid substrate. In cases where the substrate is a porous material, the active may be a fluid such as a flavor oil or other oleagenous material which is capable of being imbibed into the porous substrate. As will be further described herein, the substrate need not necessarily be porous in the sense of having micro-channels, but may be capable of imbibing or carrying the active, which is preferably a material which is sensitive to heat and aqueous processing conditions.

The solloid form and the flash flow process are designed to be protective of heat and solvent sensitive actives, i.e., materials such as volatile flavor oils, artificial sweeteners and drugs. The flash shear and flash heat process allow for formation of solloids which have substantially uniform shape and size as well as content of active agent. The active agent is preserved because the flash shear and flash heat processes used to produce the solloid employ conditions of temperature and force which do not jeopardize the integrity or effectiveness of the active. Compositions of the present invention are processed with little or no heat history and processing time is substantially decreased as compared to conventional spray drying and spray congealing processes. The temperatures in the flash flow process are kept as low as possible and the required heat is only that which is necessary to achieve a flowable condition of the solid fat, but insufficiently high to melt the non-fat solid substrate.

The flash flow process has distinct advantages over extrusion techniques used for spray drying and spray congealing. The present process not only eliminates the disadvantages associated with a heat history, but also eliminates the settling out of components in the mixture prior to extrusion and eliminates the dispersion agents required to prevent settling out, which are common to spray drying and congealing processes due to the melting and mixing tanks which are required. Additionally, conventional spray drying and spray congealing processes require a significant amount of physical processing room to be properly conducted. This is because since the molten fluid from the holding and mixing tank must be pumped under pressure up to a tower height such that it can be sprayed downwardly into a cool environment and allowed to dry or congeal during the free-fall. Not only is such equipment and need for larger quantities of space eliminated in the present invention, but the time period required to carry out the process is also significantly decreased. Whereas the conventional processing was batch oriented and required significant waiting times before a certain quantity of the feedstock would be pumped upward into the nozzle area, the present invention is a continuous process which has no requirement for premixing and melting of the solid fat with the non-solid, substrate. Mixtures of the inventive composition can be immediately processed in tenths of a second in the case of flash heat processing and in seconds or at most minutes in the case of flash shear processing.

The advantages of processing from solid to solid without long melting residence times are extremely important. The inventive compositions are added into either the spinning head or the extrusion barrel and processed at temperatures sufficient to allow the fat to flow. A positive pressure is maintained during the process of flash shear. This positive pressure promotes the mixture to remain stable, i.e. prevent any settling-out of the non-fat solid substrate in the fat matrix. Settling-out of mixture components is a common occurrence in spray drying and spray congealing processes. To overcome this problem, mixers are used in the holding vat. Additionally, the positive pressure in the extruder serves to promote and maintain the intimate contact between the non-fat solid substrate and the solid fat during the brief time it is in the extrusion barrel. In the case of flash heat, the process occurs under centrifugal force in essentially fractions of a second and no settling-out is likely to occur.

In the case of flash shear processing, once the composition has travelled through the extrusion barrel, it is exited through a nozzle designed to direct a disruptive force sufficient to form and maintain solloids from the flowing mixture. This force is preferably a gas stream, such as air, which is directed at the flowing mass as it exits the extruder. The disruptive force is sufficient to create the flowing stream into discrete, spheroidal particles which are substantially uniform in size and contain substantially uniform content of the active. Forces which are too great so as to strip or separate the non-fat solid substrate from the flowing fat are not contemplated as part of this invention. The force should be sufficiently great to form the solloid entity but not so great as to separate the solloid components.

In the case of flash heat processing, the spinning head is equipped with a heating element which provides sufficient temperature to cause the solid fat to flow through the apertures of the spinning heat, carrying with it the non-fat solid substrate containing the active. The flowable mass deforms sufficiently to be flung from the spinning head under centrifugal force and into the ambient atmosphere. The exiting mass is subjected to the frictional forces of ambient air as it travels from the spinning head. These frictional forces of air are sufficient to form and maintain the solloid as described herein.

The following general compositions are useful in the inventive solloid compositions and process:

| Component | % by Weight of Composition |
| --- | --- |
| Fat | 40–94 |
| Non-Fat Substrate | 5–30 |
| Active | 0.01–35 |

FIGS. 1 and 2 depict microphotographs of the present invention. FIG. 1 shows the uniformity of size and shape. FIG. 2 shows the solid non-fat substrate inside the solid fat matrix. Interstices within the fat matrix crystals are apparent from the cross-section.

Fats which are useful in the present invention are those which are substantially solid at room temperature. Hydrogenated and partially hydrogenated vegetable and animal fats are among those useful. For example, a partial listing of vegetable fats include hydrogenated or partially hydrogenated cottonseed oils, hydrogenated or partially hydrogenated soybean oils, hydrogenated or partially hydrogenated palm oils and mixtures thereof. In addition, these fats may be supplemented with the mono-, di- and triglycerides of fatty acids as well as the propylene glycol mono and diesters of fats and fatty acids. Animal fats such as tallow, lard and other hydrogenated or partially hydrogenated versions of animal fats may also be employed in the present invention.

Other matrix materials which are useful include waxes which are solid at room temperature. For example, petroleum waxes such as paraffin and microcrystalline waxes and the like may be used. These materials may be used alone or combined with the fat matrix.

Other materials may be added to the solloid compositions to modify the flow properties, texture and taste. For example, medium chain triglycerides, emulsifiers, softeners and the like may be employed. Vapor depressant additives may be added to volatile flavor oils to aid in loss of flavor components. Medium chain triglycerides have been found to be particularly useful in suppressing vaporization of menthol.

The non-fat solid substrates may be selected from a wide variety of materials which are capable of binding to, being coated with, united with or imbibing an active substance. One limitation, however, is that the melting point of the material chosen for the non-fat solid substrate must be such that it does not melt during the flash flow process. This means that the melting point of the non-fat solid substrate must be beyond the flow point temperature of the solid fat. There are several reasons for this requirement, one being that the ultimate product derived from the compositions and process of the invention is a solloid, i.e., a solid suspension of the solid substrate in the solid fat. If the substrate were allowed to melt, a blend would occur and the solid suspension would not be a solloid as defined herein. Additionally, the active agent which is associated with the solid substrate would also blend into the fat. It is the intention of the present invention to carry the active on the substrate such that it remains substantially united with the solid substrate in the solloid form. While it is entirely possible that a certain amount of active may leach out of the substrate or otherwise migrate into the flowable fat during processing, it is believed that a substantial amount of the active remains intimately associated with the substrate. The resultant solloids benefit from this characteristic in that it provides for uniformity and content of the active for each solloid, as well as a controlled release of the active therefrom. Each solloid must be disrupted by mastication, ingestion or other force such as rubbing on the skin, to release the active from the individual solloid and make it available for its intended purpose.

Representative non-fat solid substrates include, without limitation, those materials which are adsorbent as well as absorbent. For example, cellulosic materials such as alkyl celluloses, hydroxyalkyl celluloses and hydroxyalkylalkyl celluloses are contemplated. Thee include methylcellulose, hydroxymethyl cellulose, hydroxyethyl cellulose, hydroxypropyl cellulose, hydroxyethylmethyl cellulose, hydroxypropylmethyl cellulose, hydroxybutylmethyl cellulose, cellulose esters and hydroxyalkyl cellulose esters. Cellulose acetylphthalate and hydroxypropylmethyl cellulose are among those useful. Additionally, carboxyalkyl celluloses and their esters, as well as carboxyalkylalkyl celluloses and their esters are also useful. One example is carboxymethyl cellulose.

Other non-fat solid substrates include water swellable gums and mucilages, algal polysaccharides, pectin and lignin. For example, karaya gum, acacia gum, tragacanth, sodium alginate, calcium alginate, carageenen and its salts, as well as mixtures thereof may be employed. Starches, including chemically and biologically modified starches are also contemplated as being useful. Additionally, protein materials such as zein, sorghum and other prolamines may also be employed.

Various silicas and microcrystalline substances are also useful as the solid non-fat substrate. For example, silicas are well known for their ability to absorb or otherwise capture liquids and certain silicas are extremely porous in nature. For example, synthetic amorphous silica has been particularly useful since it has a unique combination of uniformity, chemical inertness, large surface area and porosity which makes it very adsorptive. These silicas are manufactured with precisely controlled surface area, porosity and particle size distribution. This makes them particularly useful in the inventive compositions. Commercially available silicas of this kind are sold under the trademarks SYLOID® and SYLOX® by W. R. Grace & Company, Baltimore, Md. These materials are specifically intended for conventional liquid dispersions and suspensions. However, they are also useful in the solid suspension of the present invention.

It is preferred that the non-fat solid substrate have mucoadhesive properties. This means that the substrate has an affinity for adhering to the mucosal membranes of the body, particularly in the mouth, such that the active can be either absorbed quickly or in the case of flavorants, perceived for long periods of time in the oral-cavity, since the active agents are carried by the substrate. These substrate materials adhere when subjected to the moist conditions of the mouth, largely because of their physical and chemical affinity to the mucosal membrane structure. The carboxyl and hydroxyl hydrophilic groups on the substrates, as well as other hydrophilic groups which may be present, are believed to be largely responsible for the affinity and adhesion of these classes of materials to the mucosal membrane. These materials also have the capability of being smooth and devoid of any unpleasant texture in the mouth. For this reason, their lubricous mouth-feel allows for them to be virtually imperceptible when bound to the mucosal surface, thereby allowing the active to be slowly released in the mouth, in the case of flavorants, or in the bloodstream in the case of drugs.

The preferred non-fat solid substrate of the present invention is hydroxypropylmethyl cellulose. This particular substrate has found to be especially useful in chewing gum compositions and other confectionery products. Flavorants such as flavor oils are generally admixed with the hydroxypropylmethyl cellulose and added to the solid fat matrix in compositions of the present invention. Since the flavor oils are readily imbibed by the cellulose, the oils are carried into the final solloid product with virtually no volatilization of the flavor components during processing.

The actives which are useful in the present invention can be chosen from any number of actives which are capable of being associated and therefore carried by the non-fat solid substrate. For example, liquids are particularly useful since they can be coated onto or imbibed by the non-fat solid substrate. However, nonliquid forms may be possible if the non-solid substrate is first flash flow processed, i.e. taking solid substrate and combining it in a flash flow process (such as described in copending U.S. Ser. No. 07/787,245, filed Nov. 4, 1991,) with solid active to form a united solid non-fat substrate/active particle.

For purposes of the present invention, however, liquids are preferred. The examples of liquid actives include drugs and oleagenous materials such as flavor oils and the like. The liquid active may be a combination of materials, such as a sweetener dissolved or dispersed in the flavor oil or a blend of two liquids. For example, artificial sweeteners can be added to the flavor oil and then imbibed onto the substrate. Alternatively, a blend of flavor oils or drug materials may be made and combined with the substrate.

In one embodiment, fish oil is coated or imbibed onto the solid non-fat substrate, e.g. starch, and incorporated into the inventive delivery system.

Flavor oils which may be useful in the present invention may be selected from a wide variety of natural or artificial oils or essences. These oils are generally derived from plant extracts, although they may alternatively be synthetically derived. Peppermint oil, spearmint oil, cinnamon oil, oil of wintergreen, menthol, citrus oils and other fruit essences are the most commonly used flavor oils which are employed in the present invention. The solloids of the present invention give the perception that a greater quantity of flavor is present than the actual amount, thereby enhancing both the organoleptic impact with less flavor oil and eliminating the need for higher amounts of flavor oil or active. This is particularly useful in applications such as chewing gum compositions, where the addition of flavor oil at high concentrations to achieve a more intense flavor impact results in plasticization of the gum base components and sloppy chew characteristics. Additionally, flavor oils such as peppermint oil, spearmint oil, menthol and cinnamon oil are particularly harsh and create a burning sensation in the mouth if ingested in too high a quantity. The present invention allows for the use of smaller quantities than in typically comestible applications if desired, with the perception that greater quantities are present.

Alternatively, because the process allows for precision in the amount of active in the solloid, higher loading of the active than in prior methods is possible. In essence, the processes of the present invention allow for precise control of the quantity of active in the solloid.

Examples of citrus or first oils and/or essences which are useful include a host of materials such as apple, apricot, banana, blueberry, cherry, grape, grapefruit, lemon, lime, orange, pear, peaches, pineapple, plum, raspberry, strawberry and the like. Mixtures and derivatives of these materials are contemplated.

Additional flavoring agents may be chosen from synthetic flavor oils and flavoring aromatics, and/or oils, oleo resins and extracts derived from plants, leaves, flowers, fruits and so forth, and combinations thereof. For example, clove oil, bay oil, anise oil, eucalyptus oil, thyme oil, cedar leaf oil, oil of nutmeg, oil of sage, oil of bitter almonds and cassia oil may be used. Commonly used flavors include menthol, artificial vanilla, cinnamon derivatives, and various fruit flavors, whether employed individually or in admixture.

Flavorings such as aldehydes and esters including cinnamyl acetate, cinnamaldehyde, citral diethylacetal, dihydrocarvyl acetate, eugenyl formate, p-methylamisol, and so forth may also be used. Generally any flavoring or food additive such as those described in "Chemicals Used in Food Processing," pub 1274 by the National Academy of Sciences, pages 63–258 may be used.

Further examples of aldehyde flavorings include, but are not limited to acetaldehyde (apple); benzaldehyde (cherry, almond), anisic aldehyde (licorice, anise); cinnamic aldehyde (cinnamon); citral, i.e., alpha citral (lemon, lime); neral, i.e. beta citral (lemon, lime); decanal (orange, lemon); ethyl vanillin (vanilla, cream); hellotropine, i.e., piperonal (vanilla, cream); vanillin (vanilla, cream); alpha-amyl cinnamaldehyde (spicy fruity flavors); butyraldehyde (butter, cheese); valcraldehyde (butter, cheese); citronellal; decannal (citrus fruits); aldehyde C-8 (citrus fruits); aldehyde C-9 (citrus fruits); aldehyde C-12 (citrus fruits); 2-ethylbutyraldehyde (berry fruits); hexenal, i.e., trans-2 (berry fruits); tolyl aldehyde (cherry, almond); veratraldehyde (vanilla); 2,6-dimethyl-5-heptenal, i.e. melonal (melon); 2,6-dimethyloctanal (green fruit); and 2-dodecenal (citrus, mandarin), mixtures thereof and the like.

Other specific flavor compounds such as ethylacetate, thiophene, ethylpropionate, ethyl butyrate, 2-hexanoate, 2-methylpyazine, heptaldehyde, 2-octanone, limonene, and eugenol are also useful.

The flavor oil content of the present delivery systems is generally in the range of about 0.02% to about 40% by weight of the delivery system. However, deviations from this range are certainly possible provided that the solloid is formed as a result of the flash flow process. Preferably, the oils are present in amounts of about 0.5% to about 20% by weight of the solloid delivery system and most preferably about 2% to about 12%.

Those drugs which may be useful in the present invention include either solid or liquid drugs which may be combined with the non-fat solid substrate. Liquids are preferred since they can be imbibed or otherwise coated onto the substrate. However, as previously discussed above, solids may be combined with the non-fat solid substrate via flash flow processing to form a new solid form which can be incorporated in the compositions of the present invention.

The drugs useful may be selected from a wide range of drugs and their acid addition salts. These drugs can be used either singly or in combination. Both inorganic and organic salts may be used provided the drug maintains its medicament value. Exemplary acid salts include hydrochloride, hydrobromide, orthophosphate, benzoate, maleate, tartrate, succinates, citrate, salicylate, sulfate, and acetate. The weight percent of the drug in the mixture which is formed into solloids is up to about 30% by weight.

One advantage of the present invention is that the active in the solloid product is in substantially the same proportion as it is in the mixture. This is particularly useful in dosage forms where the active content is critical. For example, the solloids containing the active can be used to fill a pharmaceutical capsule.

Final dosage forms in which the solloids may be present can be selected from any number of vehicles or dosage forms. For example, food products, medicaments, baked goods, pharmaceutical preparations, lozenges, capsules, nuggets, chewing gum, liquids and gels may be employed among others.

Once prepared, the solloids may be stored for future use or formulated with conventional additives such as pharmaceutically acceptable carriers and confectionery ingredients to prepare compositions which offer a variety of textures to suit particular applications. Pharmaceutically acceptable carriers may be selected from a wide range of materials. Without being limited thereto, such materials include diluents, binders and adhesives, lubricants, disintrigants, colorants, flavorings, sweeteners and other miscellaneous materials such as buffers and adsorbents used to prepare a particular medicated composition. In addition, elixirs, and syrups whereby the solloids are suspended therein are also contemplated.

Among the drugs which are useful, include the following:

(a) Antitussives, such as dextromethorphan, dextromethorphan hydrobromide, noscapine, carbetapentane citrate, and chlorphedianol hydrochloride;

(b) Antihistamines, such as chlorpheniramine maleate, phenindamine tartrate, pyrilamine maleate, doxylamine succinate, and phenyltoloxamine citrate;

(c) Decongestants, such as phenylephrine hydrochloride, phenylpropanolamine hydrochloride, pseudoephedrine, hydrochloride ephedrine;

(d) Various alkaloids, such as codeine phosphate, codeine sulfate and morphine;

(e) Mineral and nutritional supplements such as potassium chloride and calcium carbonates, magnesium oxide and other alkali metal and alkaline earth metal salts;

(f) Laxatives, vitamins and antacids;

(g) Ion exchange resins such as cholestyramine;

(h) Anti-cholesterolemic and anti-lipid agents;

(i) Antiarrhythmics such as N-acetylprocainamide;

(j) Antipyretics and analgesics such as acetaminophen, aspirin and ibuprofen;

(k) Appetite suppressants such a phenylpropanolamine hydrochloride or caffeine; and (l) Expectorants such as guaifenesin; and (m) $H_2$ inhibitors.

Additional useful active medicaments include anti-inflammatory substances, coronary dilators, cerebral dilators, peripheral vasodilators, anti-infectives, psycho-tropics, antimanics, stimulants, gastro-intestinal sedatives, antidiarrheal preparations, anti-anginal drugs, vasodilators, anti-hypertensive drugs, vasoconstrictors and migraine treatments, antibiotics, tranquilizers, antipsychotics, antitumor drugs, anticoagulants and antithrombotic drugs, hypnotics, sedatives, antiemetics, antinauseants, anticonvulsants, neuromuscular drugs, hyper- and hypoglycemic agents, thyroid treatment preparations, diuretics, antispasmodics, uterine relaxants, antiobesity drugs, anabolic drugs, erythropoietic drugs, antiasthmatics, expectorants, mucolytics, anti-uricemic drugs, and the like.

Mixtures of the drugs and medicaments may also be used.

The present invention contemplates the inclusion of those sweeteners well known in the art, including both natural and artificial sweeteners. Thus, sweeteners may be chosen from the following non-limiting list; sugars such as sucrose, glucose (corn syrup), dextrose, invert sugar, fructose, and mixtures thereof; saccharin and its various salts such as the sodium or calcium salt; cyclamic acid and its various salts such as the sodium or calcium salt; the dipeptide sweeteners such as aspartame and alitame; chlorinated sugar derivatives such as sucralose; natural sweeteners such as dihydrochalcone; glycyrrhin; Stevia rebaudiana (Stevioside); and sugar alcohols such as sorbitol, sorbitol syrup, mannitol, xylitol, and the like. Also contemplated as a sweetener is the nonfermentable sugar substitute hydrogenated starch hydrolysate (lycasin) which is described in U.S. Pat. No. Re. 26,959. Also contemplated is the synthetic sweetener 3,6-dihydro-6-methyl-1-1,2,3 -oxathiazin-4-one-2, 2-dioxide particularly the potassium (Acesulfame-K), sodium and calcium salts thereof as described in German Patent No. 2,001,017.7.

The sweeteners may be incorporated as the active agent, per se, i.e., flash flow processed with the non-fat solid substrate to form a substrate/active combined solid, combined with a flavor oil as the active or incorporated directly in the fat matrix.

The delivery system can be incorporated in conventional chewing gum compositions. These compositions typically contain a sweetener, a gum base and a flavor. Additionally sources of flavor and/or sweetener can of course be combined with the solloid delivery system and incorporated in the chewing gum composition.

In the present invention, the flavor, sweetener and optionally acidulants can be incorporated into the solloid. For example, in one embodiment a flavorant selected from the group consisting of flavor oils, sweeteners, food acids (also referred to as acidulants), and mixtures thereof may be united with the solid non-fat substrate. Preferably a mixture of all three are present. In another embodiment, one or more of the flavorant materials may additionally be incorporated into the solid fat matrix such that it remains in the solid fat portion of the solloid.

Chewing gum compositions incorporating the novel solloid delivery systems have distinct advantages in terms of other flavorant material. Once incorporated into a chewing gum composition, the solloid form serves to protect the flavorants from other components in the chewing gum as well as preventing migration of the flavorant from the gum base onto the surface of the gum.

One particular advantage to the inventive delivery systems relates to their ability to sustain the flavor and sweetness perception of the chewing gum. The non-fat solid substrate preferably has a muco-adhesive property which serves to adhere the solloids to the mucous membranes of the mouth. The solloids slowly release their flavorant materials through a delayed hydradation process. The perception of flavor and sweetness is significantly increased due to the presence of the solloids in the mouth during mastication.

As a demonstration of the comparative sustained release of flavor and sweetness of the present inventive chewing gum compositions containing the novel solloids as compared to commercially available chewing gum compositions can be demonstrated by the following data. This data was developed by an expert chewing panel and ratings were based on a scale of 1–10 with 1 being the lowest rating and 10 being the highest rating.

FLAVOR AND SWEETNESS DURATION EVALUATION
COMMERCIALLY AVAILABLE PRODUCTS vs. INVENTIVE PRODUCT

|  | Amount of Flavor | | | Amount of Sweetness | | |
|---|---|---|---|---|---|---|
| Time | Wrigley's Peppermint | Extra ® Peppermint | Inventive Peppermint | Wrigley's Peppermint | Extra ® Peppermint | Inventive Peppermint |
| 0.30 Seconds | 8.00 | 7.42 | 8.86 | 8.14 | 8.29 | 8.71 |
| 5.0 Minutes | 5.43 | 5.86 | 8.57 | 5.29 | 5.57 | 8.00 |
| 10.0 Minutes | 3.43 | 4.86 | 7.71 | 3.00 | 3.86 | 6.43 |
| 15.0 Minutes | 2.00 | 4.12 | 7.00 | 1.29 | 3.14 | 5.29 |
| 20.0 Minutes | 0.86 | 3.14 | 5.57 | 0.57 | 2.71 | 4.14 |
| 25.0 Minutes | 0.29 | 2.14 | 4.00 | 0.29 | 2.14 | 3.57 |
| 30.0 Minutes | 0.14 | 1.86 | 3.86 | 0.14 | 1.43 | 3.00 |
| 40.0 Minutes | 0.00 | 0.86 | 3.43 | 0.00 | 0.57 | 2.71 |
| 50.0 Minutes | 0.00 | 0.29 | 2.86 | 0.00 | 0.29 | 2.00 |
| 60.0 Minutes | 0.00 | 0.29 | 2.29 | 0.00 | 0.14 | 1.71 |

FLAVOR AND SWEETNESS LIKING EVALUATION
COMMERCIALLY AVAILABLE PRODUCTS vs. INVENTIVE PRODUCT

|  | Flavor Liking | | | Sweetness Liking | | |
|---|---|---|---|---|---|---|
| Time | Wrigley's Peppermint | Extra ® Peppermint | Inventive Peppermint | Wrigley's Peppermint | Extra ® Peppermint | Inventive Peppermint |
| 0.30 Seconds | 7.43 | 6.71 | 8.29 | 7.71 | 6.57 | 8.29 |
| 05.0 Minutes | 4.86 | 5.43 | 8.43 | 5.57 | 5.14 | 8.00 |
| 10.0 Minutes | 3.14 | 4.14 | 7.43 | 2.86 | 4.00 | 7.29 |
| 15.0 Minutes | 1.43 | 3.00 | 6.71 | 1.00 | 3.00 | 6.29 |
| 20.0 Minutes | 0.43 | 2.43 | 5.14 | 0.43 | 2.57 | 4.86 |
| 25.0 Minutes | 0.14 | 1.86 | 4.29 | 0.14 | 1.86 | 4.14 |
| 30.0 Minutes | 0.14 | 1.57 | 3.86 | 0.14 | 1.43 | 3.71 |
| 40.0 Minutes | 0.00 | 0.86 | 3.57 | 0.00 | 0.57 | 2.86 |
| 50.0 Minutes | 0.00 | 0.29 | 2.86 | 0.00 | 0.29 | 2.00 |
| 60.0 Minutes | 0.00 | 0.14 | 2.14 | 0.00 | 0.14 | 1.71 | sustained flavorant perception. Due to the physical structure of the solloid, the flavorant materials are protected during processing as well as in the bulk storage form subsequent to processing. The fat surrounding the non-fat solid substrate serves to prevent volatilization of the flavorant materials from the discrete solloid particles as well as to prevent moisture from prematurely attacking the sweetener and/or The first evaluation table above relates to the sweetness and flavor duration. The expert panel was given samples of commercially available chewing gum products, namely Wrigley's Peppermint and Wrigley's Extra® Peppermint chewing gums and asked to compare these to the inventive peppermint chewing gums. Samples of each of the chewing gum products were chewed by all members of the panel. The gums were masticated for a sixty minute period, with ratings taken at the intervals listed in the tables. It is abundantly clear from the duration evaluation table that while the commercially available chewing gum products have flavor and sweetness duration at the 30 second level which is substantially similar to those of the inventive products, the ratings for the commercially available products drop significantly even after 5 minutes. At the 10 minute mark, the ratings for the two commercially available products with respect to both flavor and sweetness were only half as good as the flavor ratings given to the inventive products. The ratings were substantially greater in the inventive compositions after 30–60 minutes of chew. More specifically, at the 60 minute level, the inventive products were ten times or more greater in flavor and sweetness, as evidenced from the tables.

With respect to the flavor and sweetness liking evaluation, reference is made to the second table above. "Liking" is the term used for overall pleasure sensation received during chew. Liking substantially dropped off in the commercially available products after 5 minutes of chewing. This is compared to the liking ratings for the inventive products which stayed substantially the same even after 10–15 minutes of chewing. At the 25 minute mark, the inventive compositions showed ratings of 4.29 (flavor) and 4.14 (sweetness), while the commercially available chewing gum products were only 0.14 and 1.57 for flavor and 0.14 and 1.43 for sweetness. No substantial flavor or sweetness was perceived at the 40 minute mark for the original Wrigley's Peppermint gum, and liking ratings of 0.86 and 0.57 were given for the Extra Peppermint gum at those time periods. However, the present inventive compositions produced chewing gums which produced ratings substantially higher at the 30–60 minute mark, 2.14–3.86 (flavor) and 1.71–2.86 (sweetness), indicating perception of the flavor and sweetness was clearly present and still enjoyable.

The ability of chewing gum to retain its flavor and sweetness after 60 minutes or more of chewing is believed to be due in part to the ability of the solloids to be retained in the mouth, allowing the sensation and perception of the flavorants to be prolonged.

With regard to chewing gum compositions, the amount of gum base employed will vary greatly depending on various factors such as the type of base, consistency desired and other components used to make the final product. In general, amounts of about 5% to about 85% by weight of the final chewing gum compositions are acceptable, with amounts of about 15% to about 30% by weight being preferred. The gum base may be any water-insoluble gum base well known in the art. Illustrative examples of suitable polymers in gum bases include both natural and synthetic elastomers and rubbers. For example, those polymers which are suitable in gum bases include, without limitation, substances of vegetable origin such as chicle, jelutong, gutta percha and crown gum. Synthetic elastomers such as butadiene-styrene copolymers, isobutylene-isoprene copolymers, polyethylene, polyisobutylene, polyvinylacetate and mixtures thereof are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene; terpene resins including polyterpene and mixtures thereof. The solvent may be employed in an amount ranging from about 10% to about 75% and preferably about 45% to about 70% by weight of the gum base.

A variety of traditional ingredients such as plasticizers or softeners such as lanolin, stearic acid, sodium stearate, potassium stearate, glycerol triacetate, glycerin and the like, including, natural waxes, such as paraffin waxes and microcrystalline waxes may also be incorporated into the gum base to obtain a variety of desirable textures and consistency properties. In accordance with the invention, however, these ingredients may be reduced in amount or in some cases, may be eliminated entirely. When present, these individual additional materials are generally employed in amounts of up to about 15% by weight and preferably in amounts of from about 3% to about 10% by weight of the final gum base composition.

The chewing gum may additionally include the conventional additives of coloring agents such as titanium dioxide; emulsifiers such as lecithin and glycerol monostearate; additional fillers such as aluminum hydroxide, alumina, aluminum silicates; calcium carbonate, and talc and combinations thereof; and additional flavoring agents. These fillers may also be used in the gum base in various amounts. Preferably, the amount of fillers when used will vary from about 4% to about 35% by weight of the final chewing gum.

The amount of solloid delivery system used in the chewing gum composition will largely be a matter of preference. It is contemplated that the delivery system will be included in amounts of from about 0.25% to about 40% by weight of the final gum composition, with amounts of from about 1% to about 30% being preferred, and amounts of from about 1% to about 20% being most preferred.

In addition to the inventive delivery system, the chewing gum composition may also optionally include one or more additional ingredients such as conventional polysaccharide-based bulking agents including sugars or sugar alcohols, flavor delivery systems, spray-dried flavors, liquid flavors, natural and/or artificial sweeteners and the like.

The chewing gum compositions of the present invention may be prepared by combining the water-insoluble gum base portion and the water-soluble flavor portion including the novel flavor/sweetener delivery system according to conventional chewing gum processing techniques.

For illustrative purposes, a method of preparing the novel chewing gum compositions is as follows:

A suitable chewing gum base is first melted. Softeners and bulking agents such as sugars or sugar alcohols if desired may be added slowly with stirring thereafter. The inventive delivery system is then added and mixing is continued until a homogeneous mass is achieved. Optionally, additional flavor oils or spray dried flavors may be added as well. The mass may then be rolled, scored, dusted and wrapped in any manner known in the art.

With regard to the preparation of other types of comestibles, the inventive solloid delivery system may also be added in a conventional manner. For example, in the case of pressed tablets, the delivery system may be dry blended with the remaining tablet ingredients and the mixture thereafter compressed into final tablet forth. In the case of dentifrices, denture creams and cleansers, the products also benefit from incorporation of the delivery system in their formulations. In short, the matrix may be added to various comestibles in a manner similar to that which the skilled artisan currently uses to add conventional comestible ingredients.

In one particular embodiment, a micron-sized synthetic, amorphous silica has been used as the non-fat solid substrate for liquid actives. Using these materials, flavor oils can be adsorbed onto their surfaces and into their pores and the added to the feedstock of matrix material to form the inventive delivery systems. In this manner, additional controlled release characteristics can be imparted to the delivery systems, as well as adding further stabilization and protective features to the oils against volatilization and oxidation. These silica compounds also have ionic and hydrogen bond affinity for certain flavor component chemical groups, which affinity serves to strengthen flavor retention and consequently allows for increased delayed release capabilities and stabilization characteristics.

In another embodiment, polyunsaturated fatty acids such as fish oil are combined with a starch non-fat solid substrate and added to the fat matrix.

Additional materials which can be used as carriers for the flavor oils prior to incorporation with the inventive delivery system include maltodextrins, such as spray-dried maltodextrin marketed under the tradename M100 (10 DE) by Grain Processing Corporation, Muscatine, Iowa, as well as agglomerated maltodextrin (10 DE) sold under the tradename Micropor Buds 1015A, by E. Staley Manufacturing Co., Decatur, Ill. These materials are also porous and allow for flavor retention. Polydextrose and microcrystalline cellulose are also useful in this regard, as are a number of other adsorbent materials.

EXAMPLES

The following examples serve to provide further appreciation of the invention, but are not meant in any way to restrict the effective scope of the invention.

The following compositions were used to produce solloids in both the flash shear and flash heat processes.

| | Solloid Delivery System Composition (% wt) | | |
|---|---|---|---|
| Component | A | B | C |
| Partially Hydrogenated Soybean Oil | 58.08 | 66.00 | 66.00 |
| HPMC[1] | 15.00 | 10.00 | 10.00 |
| Flavor Oil | 12.50* | 10.00* | 10.00** |
| Artificial Sweetener | 10.42 | 10.00 | 10.00 |
| Optional Ingredients[2] | 4.00 | 4.00 | 4.00 |

[1]hydroxypropylmethyl cellulose
[2]emulsifier and fillers
*spearmint/peppermint blend
**peppermint oil/menthol blend Flash Shear Process Each of the above compositions were processed using flash shear processing to yield the inventive solloid delivery system. Each composition was prepared as a mixture. The respective composition mixtures were then individually processed using an extruder where the extrudate was subjected to disrupted air flow, with an atomizing nozzle. The compositions were fed into a twin screw extruder and the feed rate adjusted to maximize product quality.

The flash shear parameters of compositions A–C are shown in the following table.

| Composition | Extruder System Temp °C. | Screw Speed rpm | Nozzle Air Pressure psig | Nozzle Air Temp °C. |
|---|---|---|---|---|
| A | 62–70 | 309 | 2.25 | 75 |
| B | 70 | 310 | 2.5 | 79 |
| C | 70 | 300 | 2.5 | 80 |

The compositions were exposed to temperatures sufficient to cause them to flow, which as shown in the table below was about 62°–70° C. for partially hydrogenated soybean oil. The screw speed used was between about 300–310 rpm's, but this speed is only limited by the speed capacity of the machine. Higher speeds such as 500 rpm's or more have been successfully run. As a general principal, the higher the screw speed, the faster the throughput of the extrudate, and the shorter the residence time. In the compositions below, the residence time of the mixture in the extruder was between about 60–83 seconds. Residence time will of course vary depending on a number of factors, but for purposes of the present invention, the residence time of the composition need only be long enough for the fat to reach its intraparticle flow point. As described in the specification above, this will vary depending on the fat used. With small extrusion machines, the residence time may be as short as 5 seconds, whereas with large production equipment it may be closer to 160 seconds. In the above compositions the temperature of the fat while in the extruder system was between about 62°–70° C., but the inventive process need only use temperatures which are sufficient to cause the fat to undergo intraparticle flow which for some materials, depending upon the pressure and other parameters, may be lower than its melting point. In any event, this temperature must be below the melting point of the non-fat solid substrate and preferably no greater than about 10° C. above the fat melting point.

The material processed in the extruder is ejected through a nozzle which has air streams directed against it to disrupt the extrudate into small solloid particles. A nozzle which provides a concentric flow of air around the flow of extrudate and two banks of three opposed air jets directed at the extrudate and the concentric air flow have been used to provide a uniform size distribution of solloid particles when the air pressure is as set forth in the above table.

As compared to conventional spray congealing and spray drying processes, the process of the present invention may be considered a "cold flow" process, devoid of the long residence time in mixing and holding tanks and the various problems associated therewith. The screw speed was operated at full throttle which was between 300–310 rpm's. The air pressure was about 2.25 to about 2.5 psig.

The compositions while in the extruder system were always under a positive pressure which served to prevent settling of the non-fat solid substrate which remained in the solid state during mixing and transformation of the solid fat into the flowable state. The extruder was in this respect effectively a closed system.

The air pressure employed in process runs of the above compositions was extremely low (2.25–2.5 psig) compared to conventional spray drying or spray congealing. As mentioned above, the air pressure may be increased proportionate to nozzle orifice size. In other words, the larger the mass of flowing extrudate exiting the extruder, the more pressure which may be used and still obtain the solloid product. Although the pressures of the inventive process have been found to be extraordinarily low as compared to conventional spray drying and congealing processes, the only limitations on the quantity of disruptive force used is that it not separate the non-fat solid substrate from the fat and that it produce a solloid as defined herein. Air pressures of from 2 to 11 psig have been used successfully, although the lower pressures are preferred.

While the mass of exiting extrudate may be a relatively dense stream of flowable material, in certain instances, i.e. certain compositions and high speed production equipment, it is preferable to design the nozzle head such that the flowable extrudate exits the extruder in the form of a hollow tube. This was accomplished in the present invention using a mandrel in the nozzle orifice to direct the flowable material between the nozzle wall and mandrel in much the same manner co-extrusion extruder heads operate. The hollow "tube" of flowable extrudate was then disrupted with a stream of gas in the same manner as described herein to form solloids.

Flash Heat Process

The following example describes the flash heat process which was used to make solloids in accordance with the present invention.

A mixture of solloid Composition A above was fed into a spinning machine equipped with a heated spinning head having a heating element including a plurality of elongate openings having a height between about 0.005 and about 0.01 inches. The rotational speed of the seven inch spinning head was 3,500 rpm. Depending on the size of the spinning head and the selection of the solid fat, the rotational speed can be from about 400 to 5,000 rpm. The heating element of the spinning head was at a temperature sufficient to cause flash heat of the fat whereby the fat underwent intraparticle flow. The flow temperature for Composition A was about 70° C.

As the solid composition was flash heat processed and flung through the openings of the spinning heat into ambient air, discrete spheroidal solloids formed. As the solloids cooled in free flight the solid suspension and shape was locked-in. A sample of the solloids formed showed substantial uniformity in size and shape, with about 60% or more having a diameter in the ranges of less than about 300 to about 400 microns.

Chewing gum compositions were made in accordance with the present invention as shown in the table below. Each of the gums exhibited significant flavor and sweetness duration for periods of 60 minutes or longer.

CHEWING GUM COMPOSITIONS
(% wt)

| | 1 | 2 | 3 | 4 | 5 | 6 |
|---|---|---|---|---|---|---|
| Gum Base | 27.00 | 26.00 | 26.00 | 24.00 | 26.00 | 24.00 |
| Polyol Bulk Agent | 59.83 | 58.78 | 56.15 | 59.35 | 58.74 | 60.275 |
| Softeners/ Emulsifiers | 4.55 | 9.75 | 9.75 | 11.10 | 10.50 | 10.50 |
| Artificial Sweeteners | 0.17 | 0.17 | 0.20 | 0.05 | 0.16 | 0.725 |
| Flavor | 4.95 | 2.00 | 4.90 | 1.50 | 1.60 | 1.75 |
| Solloid Delivery System[1] | 3.50* | 3.30** | 3.00** | 4.00** | 3.00** | 2.75** |

*Spearmint
**Peppermint
[1]HPMC substrate/partially hydrogenated soybean oil (fat matrix)

The invention being thus described, it will be obvious that the same may be varied in many ways. Such variations are not to be regarded as a departure from the spirit and scope of the invention and all such modifications are intended to be included within the scope of the following claims.

While there have been described what are presently believed to be the preferred embodiments of the present invention, those skilled in the art will realize that changes and modifications may be made thereto without departing from the spirit of the invention, and it is intended to claim all such changes and modifications as fall within the true scope of the invention.

What is claimed is:

1. A method of forming a solloid for delivering actives comprising:

a) feeding to an extruder a composition comprising a non-fat solid substrate having an active associated therewith and a solid fat which is solidifiable at room temperature and having an intraparticle flow point lower than the melting point of said non-fat solid substrate;

b) subjecting said compositions in said extruder to conditions of temperature and force sufficient to cause intraparticle flow of the fat; and c) expelling said composition in a flowable state while applying a disruptive force to said composition to form discrete solids.

2. The method of claim 1, wherein the residence time of said composition in said extruder is about 5 seconds to about 120 seconds.

3. The method of claim 1 wherein the temperature of the fat in said extruder does not exceed about 10° C. above the melt point of such fat.

4. The method of claim 1, wherein said extruder is a multiple heating zone twin screw extruder.

5. The method of claim 1, wherein said disruptive force is the frictional force of a positive pressure gas stream.

6. The method of claim 5, wherein said disruptive force is provided by at least one positive pressure air stream.

7. The method of claim 5, wherein said gas stream has a temperature at least above the intraparticle flow temperature of said solid fat.

8. The method of claim 5, wherein said gas stream has a maximum temperature of about 26° C. above the intraparticle flow temperature of said fat.

9. The method of claim 5, wherein the pressure of said gas stream is about 2 psig to about 11 psig.

10. The method of claim 5, wherein the presence of said gas stream is insufficient to cause substantial separation of said solid non-fat substrate and said solid fat.

11. The method of claim 1, wherein the said extruder has a means for ejecting said composition and applying at least one stream of gas to said composition sufficient to disrupt said composition into discrete solloids.

12. The method of claim 1, wherein about 60% of said discrete solloids have a diameter in the range of about 300 to about 400 microns.

13. The method of claim 1, wherein said non-fat solid is an absorbent or adsorbent material.

14. The method of claim 13, wherein said non-fat solid is selected from the group consisting of cellulosics, silicas, microcrystalline substances, water sellable gums and mucilages, alginates, carageenans, tragacanth, starches, titanium dioxide, zein and mixtures thereof.

15. The method of claim 11, wherein said non-fat solid substrate is a muco-adhesive.

16. The method of claim 1, wherein said active is selected from the group consisting of flavorants, drugs, fragrances, coloring agents and mixtures thereof.

17. The method of claim 1, wherein the flavorant is selected from the group consisting of flavor oils, sweeteners, food acids and mixtures thereof.

18. The method of claim 1, wherein the solid fat is selected from the group consisting of hydrogenated and partially hydrogenated animal and vegetable oils and their glyceride esters.

19. The method of claim 1, wherein the intraparticle flow temperature is from about 30° C. to about 100° C.

20. The method of claim 1, wherein the percent of active in the solloid composition is about 0.1 to about 35% by weight.

21. The method of claim 1, wherein said non-fat solid substrate is hydroxypropylmethyl cellulose, said active is a flavorant and said fat is partially hydrogenated soybean oil.

22. The method of claim 17, wherein the flavorant is selected from the group consisting of peppermint oil, spearmint oil, menthol, cinnamon oil, oil of wintergreen (methylsalicylate), citrus oils, fruit essences and mixtures thereof.

23. A method of forming a solloid for delivering actives comprising:
   a) providing a composition comprising a solid non-fat substrate having an active associated therewith and a solid fat which is solidifiable at room temperature and having an intraparticle flow point lower than the melting point of said solid non-fat substrate;
   b) subjecting said composition to conditions of flash heat and disruptive force sufficient to form and maintain said solloid.

24. The method of claim 23 wherein said conditions of flash heat is provided by a heated spinning head.

25. The method of claim 24 wherein said heated spinning head includes a heating element including at least one narrow elongate opening which extends at least partially about the axis of rotation of said spinning head.

26. The solloid delivery system of claim 23, wherein the conditions of temperature and force sufficient to cause said fat to undergo intraparticle flow is provided by flash heat processing.

27. The method of claim 25, wherein the elongate opening has a height between about 0.005 and about 0.01 inches.

28. The method of claim 27, wherein the height of said elongate opening is substantially uniform throughout the length of said elongate opening.

29. The method of claim 23, wherein said flash heat occurs in less than about 2 seconds.

30. The method of claim 23, wherein the disruptive force sufficient to form and maintain said solloid is the frictional forces of ambient air.

31. The method of claim 23 wherein the temperature of the fat does not exceed about 10° C. above the melting point of said solid fat.

32. The method of claim 23, wherein said conditions of flash heat include a rotational speed of from about 400 to about 5,000 rpm.

33. The method of claim 23, wherein said solid non-fat substrate is selected from the group consisting of absorbent and adsorbent materials.

34. The method of claim 33, wherein said solid non-fat substrate is selected from the group consisting of cellulosics, silicas, microcrystalline substances, water sellable gums and mucilages, alginates, carageenans, tragacanth, starches, titanium dioxide, zein and mixtures thereof.

35. The method of claim 34, wherein said solid non-fat substrate is hydroxypropylmethyl cellulose.

36. The method of claim 23, wherein the active is selected from the group consisting of flavorants, drugs, fragrances and mixtures thereof.

37. The method of claim 36, wherein the active is selected from the group consisting of flavor oils, sweeteners, food acids and mixtures thereof.

38. The method of claim 37, wherein the flavor oil is selected from the group consisting of peppermint oil, spearmint oil, oil of wintergreen (methylsalicylate), cinnamon oil, citrus oil, fruit essences and mixtures thereof.

39. The method of claim 23, wherein the solid fat is selected from the group consisting of hydrogenated and partially hydrogenated animal and vegetable oils and their glyceride esters.

40. The method of claim 23, wherein said solloid has a diameter in the range of about 300 to about 400 microns.

* * * * *